United States Patent
Rheinheimer et al.

[11] Patent Number: 6,107,254
[45] Date of Patent: Aug. 22, 2000

[54] 5-(DIOXABICYCLOHEPT-6-YL)-CYCLOHEXENONE OXIME ETHERS, AND THE PREPARATION AND THEREOF USE

[75] Inventors: Joachim Rheinheimer; Volker Maywald, both of Ludwigshafen; Uwe Kardorff, Mannheim; Karl-Otto Westphalen, Speyer; Ulf Misslitz, Neustadt; Helmut Walter, Obrigheim, all of Germany

[73] Assignee: BASF Aktiengesellschaft, Ludwigshafen, Germany

[21] Appl. No.: 09/331,636

[22] PCT Filed: Dec. 19, 1997

[86] PCT No.: PCT/EP97/07215

§ 371 Date: Jun. 23, 1999

§ 102(e) Date: Jun. 23, 1999

[87] PCT Pub. No.: WO98/30565

PCT Pub. Date: Jul. 16, 1998

[30] Foreign Application Priority Data

Jan. 9, 1997 [DE] Germany .......................... 197 00 455

[51] Int. Cl.[7] .......................... A01N 43/16; A01N 57/16
[52] U.S. Cl. .......................... 504/292; 504/196; 549/216; 549/217; 549/396
[58] Field of Search .......................... 514/456; 549/216, 549/217, 396; 504/292, 196

[56] References Cited

U.S. PATENT DOCUMENTS

| | | | |
|---|---|---|---|
| 4,564,073 | 1/1986 | Jahn et al. | 71/88 |
| 4,812,160 | 3/1989 | Jahn et al. | 71/88 |
| 5,022,914 | 6/1991 | Kast et al. | 71/88 |
| 5,074,903 | 12/1991 | Jahn et al. | 71/90 |
| 5,190,573 | 3/1993 | Misslitz et al. | 504/292 |

*Primary Examiner*—Peter O'Sullivan
*Attorney, Agent, or Firm*—Keil & Weinkauf

[57] ABSTRACT

5-(Dioxabicyclohept-6-yl)cyclohexenone oxime ethers of the formula I

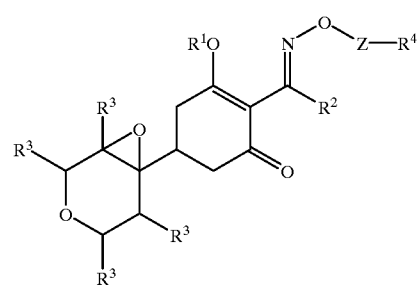

where:
$R^1$ is hydrogen, the equivalent of an agriculturally useful cation, $C_1$–$C_{10}$-alkylcarbonyl, $C_1$–$C_{10}$-alkylsulfonyl, $C_1$–$C_{10}$-alkylphosphonyl, benzoyl, benzenesulfonyl or benzenephosphonyl;
$R^2$ is $C_1$–$C_6$-alkyl;
$R^3$ is in each case, independently of the others, hydrogen or $C_1$–$C_4$-alkyl;
Z is a $C_1$–$C_6$-alkylene, $C_3$–$C_6$-alkenylene or $C_3$–$C_6$-alkynylene chain which may carry an exo-methylene substituent (=CH$_2$) and/or in each case one to three additional substituents selected from the group consisting of $C_1$–$C_3$-alkyl substituents and halogen atoms,
is a $C_3$—$C_6$-alkylene or $C_4$—$C_6$-alkenylene chain which may carry one to three $C_1$–$C_3$-alkyl substituents and which contains, in addition to methylene or methine units, one of the following bridge members: oxygen, sulfur, —SO—, —SO$_2$— or —N($R^i$)—, where $R^i$ is hydrogen, $C_1$–$C_4$-alkyl, $C_3$–$C_6$-alkenyl or $C_3$–$C_6$-alkynyl;
$R^4$ is hydrogen, halogen or phenyl, where the phenyl group may be unsubstituted, partially or fully halogenated and may carry, if it is not fully halogenated, one to three substituents which are as defined in the claims,
and the preparation and use thereof.

9 Claims, No Drawings

5-(DIOXABICYCLOHEPT-6-YL)-CYCLOHEXENONE OXIME ETHERS, AND THE PREPARATION AND THEREOF USE

This application is a 371 of PCT/EP97/07215 filed Dec. 19, 1997.

DESCRIPTION

The present invention relates to novel 5-(dioxabicyclohept-6-yl)cyclohexenone oxime ethers of the formula I

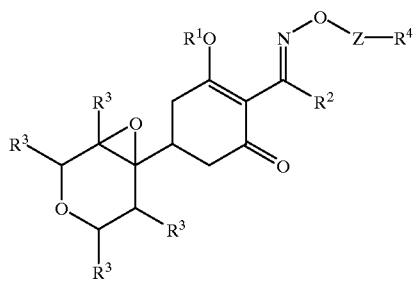

where $R^1$ is hydrogen, the equivalent of an agriculturally useful cation, $C_1$–$C_{10}$-alkylcarbonyl, $C_1$–$C_{10}$-alkylsulfonyl, $C_1$–$C_{10}$-alkylphosphonyl, benzoyl, benzenesulfonyl or benzenephosphonyl, where the last three radicals may additionally carry 1 to 5 halogen atoms;

$R^2$ is $C_1$–$C_6$-alkyl;

$R^3$ is in each case, independently of the others, hydrogen or $C_1$–$C_4$-alkyl;

Z is a $C_1$–$C_6$-alkylene, $C_3$–$C_6$-alkenylene or $C_3$–$C_6$-alkynylene chain which may carry an exo-methylene substituent (=CH$_2$) and/or in each case one to three additional substituents selected from the group consisting of $C_1$–$C_3$-alkyl substituents and halogen atoms,
is a $C_3$–$C_6$-alkylene or $C_4$–$C_6$-alkenylene chain which may carry one to three $C_1$–$C_3$-alkyl substituents and which contains, in addition to methylene or methine units, one of the following bridge members: oxygen, sulfur, —SO—, —SO$_2$— or —N($R^i$)—, where $R^i$ is hydrogen, $C_1$–$C_4$-alkyl, $C_3$–$C_6$-alkenyl or $C_3$–$C_6$-alkynyl;

$R^4$ is hydrogen, halogen or phenyl, where the phenyl group may be unsubstituted, partially or fully halogenated and may carry, if it is not fully halogenated, one to three substituents selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-alkenyl, $C_3$–$C_6$-alkenyloxy, $C_3$–$C_6$-alkynyl, $C_3$–$C_6$-alkynyloxy and —NR$^5$R$^6$, where $R^5$ is $C_1$–$C_4$-alkyl, $C_3$–$C_6$-alkenyl or $C_3$–$C_6$-alkynyl and $R^6$ is $C_1$–$C_4$-alkyl, $C_3$–$C_6$-alkenyl, $C_3$–$C_6$-alkynyl, $C_1$–$C_6$-acyl or benzoyl, which may carry one to three additional substituents selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio.

The invention additionally relates to herbicidal compositions and plant-growth regulating compositions comprising the compounds I as active substances, a process for preparing the compounds I, intermediates of the formula II, a method for controlling undesirable vegetation using the compounds I, the use of the compounds I as herbicides and for regulating the growth of plants.

Herbicidally active cyclohexenone oxime ethers having a tetrahydropyran-4-yl radical in position 5 of the cyclohexenone ring are known from the literature (EP-A 142 741, DE-A 38 38 309 and EP-A 456 112).

EP-A 230 235 describes herbicidally active 5-(3,7-dioxabicyclo[4.1.0]hept-1-yl)cyclohexenone oximes which differ from the compounds according to the invention in that the bicycle is linked in position 1 instead of position 6.

The herbicidal properties of the prior art compounds with regard to their activity and in particular with regard to their selectivity against grass weeds in grass-like crops are not always entirely satisfactory.

It is an object of the present invention to provide novel herbicidally active cyclohexenone oximes. It is a further object to provide novel growth-regulating compounds.

We have found that this object is achieved by the novel 5-(dioxabicyclohept-6-yl)cyclohexenone oxime ethers I defined at the outset. Furthermore, we have found herbicidal and growth-regulating compositions comprising the compounds I, processes for preparing the compounds I and intermediates of the formula II required for their preparation, a method for controlling undesirable vegetation using the compounds I and the use of the compounds I as herbicides and growth regulators.

Depending on the substitution pattern, the compounds of the formula I can contain one or more chiral centers, in which case they exist in the form of enantiomer or diastereomer mixtures. The invention provides the pure enantiomers or diastereomers and also the mixtures thereof.

The moieties mentioned in the definition of the radicals $R^1$ to $R^6$ and Z or as substituents of alkyl, alkenyl, alkynyl and phenyl are collective terms for individual listings of the individual group members. The radicals alkyl, alkylthio, alkoxy, alkylcarbonyl, alkylsulfonyl, alkylphosphonyl, alkenyl, alkenyloxy, alkynyl and alkynyloxy can be straight-chain or branched. The unsubstituted alkylene, alkenylene and alkynylene chains are straight-chain. Halogenated substituents preferably have attached to them one to three identical or different halogen atoms. The term halogen represents in each case bromine, iodine, and in particular fluorine or chlorine.

Other examples of meanings are:

$C_1$–$C_4$-alkyl, and the alkyl moieties of $C_1$–$C_4$-alkylthio: methyl, ethyl, propyl, 1-methylethyl, butyl, 1-methylpropyl, 2-methylpropyl and 1,1-dimethylethyl;

$C_1$–$C_6$-alkyl: $C_1$–$C_4$-alkyl as mentioned above, and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-alkoxy: methoxy, ethoxy, propoxy, 1-methylethoxy, butoxy, 1-methylpropoxy, 2-methylpropoxy and 1,1-dimethylethoxy;

$C_1$–$C_4$-haloalkoxy: a $C_1$–$C_4$-alkoxy radical as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_{10}$-alkyl of the alkyl moieties of $C_1$–$C_{10}$-alkylcarbonyl, $C_1$–$C_{10}$-alkylsulfonyl and $C_1$–$C_{10}$-alkylphosphonyl: methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, heptyl, octyl, 2-ethylhexyl, nonyl, decyl;

agriculturally useful cation: alkali metal salts, in particular the sodium or potassium salt, alkaline earth metal salts, in particular the calcium, magnesium or barium salt, the manganese, copper, zinc or iron salt and the ammonium, phosphonium, sulfonium or sulfoxonium salts, for example ammonium salts, tetraalkylammonium salts, benzyltrialkylammonium salts, trialkylsulfonium salts or trialkylsulfoxonium salts;

$C_3$–$C_6$-alkenyl and the alkenyl moieties of $C_3$–$C_6$-alkenyloxy: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-2-en-1-yl, 1,2-dimethylbut-3-en-1-yl, 1,3-dimethylbut-2-en-1-yl, 1,3-dimethylbut-2-en-1-yl, 1,3-dimethylbut-3-en-1-yl, 2,2-dimethylbut-3-en-1-yl, 2,3-dimethylbut-3-en-1-yl, 2,3-dimethylbut-2-en-1-yl, 2,3-dimethylbut-3-en-1-yl, 3,3-dimethylbut-2-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_3$–$C_6$-alkynyl and the alkynyl radicals of $C_3$–$C_6$-alkynyloxy: prop-1-in-1-yl, prop-2-in-1-yl, but-1-in-1-yl, but-1-in-3-yl, but-1-in-4-yl and but-2-in-1-yl; pent-1-in-1-yl, pent-1-in-3-yl, pent-1-in-4-yl, pent-1-in-5-yl, pent-2-in-1-yl, pent-2-in-4-yl, pent-2-in-5-yl, 3-methylbut-1-in-3-yl, 3-methylbut-1-in-4-yl, hex-1-in-1-yl, hex-1-in-3-yl, hex-1-in-4-yl, hex-1-in-5-yl, hex-1-in-6-yl, hex-2-in-1-yl, hex-2-in-4-yl, hex-2-in-5-yl, hex-2-in-6-yl, hex-3-in-1-yl, hex-3-in-2-yl, 3-methylpent-1-in-1-yl, 3-methylpent-1-in-3-yl, 3-methylpent-1-in-4-yl, 3-methylpent-1-in-5-yl, 4-methylpent-1-in-1-yl, 4-methylpent-2-in-4-yl and 4-methylpent-2-in-5-yl;

$C_1$–$C_6$-alkylene: the straight-chain alkylene chains methylene, ethylene, propylene, butylene, pentylene and hexylene, it being possible for these chains to carry an exo-methylene substituent and/or in each case one to three additional substituents selected from the group consisting of $C_1$–$C_3$-alkyl substituents and halogen atoms;

$C_3$–$C_6$-alkenylene: the straight-chain alkenylene chains, such as, for example, 2-propenylene, 2-butenylene, 3-butenylene, 2-pentenylene, it being possible for these chains to carry an exo-methylene substituent and/or in each case one to three additional substituents selected from the group consisting of $C_1$–$C_3$-alkyl substituents and halogen atoms;

$C_3$–$C_6$-alkynylene: the straight-chain alkynylene chains, such as, for example, 2-propynylene, 2-butynylene, 3-butynylene, 2-pentynylene, it being possible for these chains to carry an exo-methylene substituent and/or in each case one to three additional substituents selected from the group consisting of $C_1$–$C_3$-alkyl substituents and halogen atoms;

a $C_3$–$C_6$-alkylene chain which contains, in addition to methylene units, one of the following bridge members: oxygen, sulfur, —SO—, —SO$_2$— or —N(R$^i$)—: 3-oxapropylene, 3-azapropylene, 3-thiapropylene, 3-thiapropylene-3-oxide, 3-thiapropylene-3,3-dioxide, 3-oxabutylene, 3-azabutylene, 3-thiabutylene, 3-thiabutylene-3-oxide, 3-thiabutylene-3,3-dioxide, 4-oxabutylene, 4-azabutylene, 4-thiabutylene, 4-thiabutylene-4-oxide, 4-thiabutylene-4,4-dioxide, 3-oxapentylene, 3-azapentylene, 3-thiapentylene, 3-thiapentylene-3-oxide, 3-thiapentylene-3,3-dioxide, 4-oxapentylene, 4-azapentylene, 4-thiapentylene, 4-thiapentylene-4-oxide, 4-thiapentylene-4,4-dioxide, 5-oxapentylene, 5-azapentylene, 5-thiapentylene, 5-thiapentylene-5-oxide, 5-thiapentylene-5,5-dioxide.

Particular preference is given to 3-oxapropylene, 3-oxabutylene and 4-oxabutylene, it being possible for these and for the other abovementioned alkylene chains to carry one to three $C_1$–$C_3$-alkyl substituents, in particular one to three methyl substituents;

a $C_4$–$C_6$-alkenylene chain which contains, in addition to methine units, one of the following bridge members: oxygen, sulfur, —SO—, —So$_2$— or —N(R$^i$)—, for example: 5-oxapent-3-enylene, 5-azapent-3-enylene, 5-thiapent-3-enylene, it being possible for these chains to carry one to three $C_1$–$C_3$-alkyl substituents, in particular one to three methyl substituents.

With regard to the herbicidal activity of the 5-(dioxabicyclohept-6-yl)cyclohexenone oxime ethers I, particular preference is given to the following meanings of the substituents, in each case either on their own or in combination:

$R^1$ is hydrogen or the equivalent of an agriculturally useful cation, particularly preferably hydrogen, sodium, potassium, lithium or ammonium;

$R^2$ is ethyl or n-propyl;

$R^3$ is hydrogen or methyl;

Z is a $C_1$—$C_6$-alkylene, $C_3$–$C_6$-alkenylene or $C_3$–$C_6$-alkynylene chain which may in each case carry one additional $C_1$–$C_3$-alkyl substituent, is a $C_3$–$C_6$-alkylene or $C_4$–$C_6$-alkenylene chain which may carry one to three $C_1$–$C_3$-alkyl substituents and which may, in addition to methylene or methine units, contain an oxygen atom as bridge member;

$R^4$ is hydrogen, halogen or phenyl, where the phenyl group may carry one to three additional substituents selected from the group consisting of nitro, cyano, formyl, halogen, $C_1$–$C_4$-alkyl, $C_1$–$C_4$-haloalkyl, $C_1$–$C_4$-alkoxy, $C_1$–$C_4$-haloalkoxy, $C_3$–$C_6$-alkenyl, $C_3$–$C_6$-alkenyloxy, $C_3$–$C_6$-alkynyl, $C_3$–$C_6$-alkynyloxy and —NR$^5$R$^6$, where $R^5$ is hydrogen, $C_1$–$C_4$-alkyl, $C_3$–$C_6$-alkenyl or $C_3$–$C_6$-alkynyl and $R^6$ is hydrogen, $C_1$–$C_4$-alkyl, $C_3$–$C_6$-alkenyl, $C_3$–$C_6$-alkynyl, $C_1$–$C_6$-acyl or benzoyl which may carry one to three additional substituents selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio.

Particularly preferred are the following meanings, in each case either on their own or in combination:

$R^3$ is hydrogen;

Z is ethylene, propylene, 2-propenylene, 3-oxapropylene, 2-methyl-3-oxapropylene, 3-oxabutylene or 4-oxabutylene;

$R^4$ is hydrogen, halogen or phenyl which may be substituted by one or two halogen, for example chlorine or fluorine, atoms.

The 5-(dioxabicyclohept-6-yl)cyclohexenone oxime ethers of the formula I where $R^1$ is hydrogen can be drawn in a plurality of tautomeric forms, all of which are embraced by the invention (cf. formula I'):

The 5-(dioxabicyclohept-6-yl)cyclohexenone oxime ethers I are suitable, both in the form of isomer mixtures and in the form of the pure isomers, as herbicides. In general, they are tolerated by and therefore selective in broad-leaved crops, and in monocotyledonous plants which are not classified as Gramineae. In addition, some of the cyclohexenone oxime ethers I according to the invention are also suitable for the selective control of undesirable grasses in Gramineae. This effect is mainly observed at low rates of application.

Depending on the application method in question, the compounds I or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre, Ricinus communis, Saccharum officinarum, Secale cereale, Solanum tuberosum, Sorghum bicolor* (s. *vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The cyclohexenone oxime ethers I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or pouring. The use forms depend on the intended aims; in any case, they should guarantee the finest possible distribution of the active ingredients according to the invention.

Suitable inert auxiliaries are essentially: mineral oil fractions of medium to high boiling point, such as kerosene or diesel oil, furthermore coal tar oils and oils of vegetable or animal origin, aliphatic, cyclic and aromatic hydrocarbons, eg. paraffins, tetrahydronaphthalene, alkylated naphthalenes

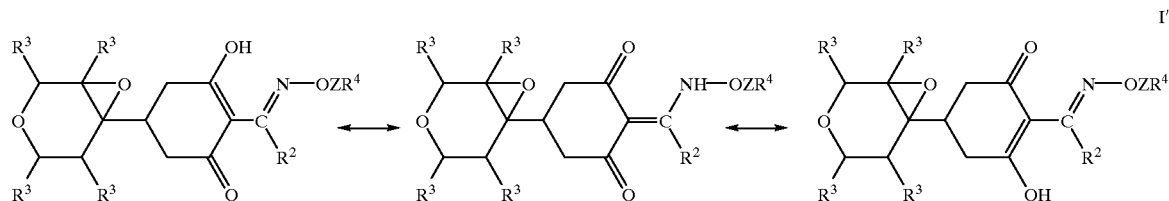

and their derivatives, alkylated benzenes and their derivatives, alcohols such as methanol, ethanol, propanol, butanol and cyclohexanol, ketones such as cyclohexanone or strongly polar solvents, eg. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, either as such or dissolved in an oil or solvent, can be homogenized in water by means of a wetting agent, tackifier, dispersant or emulsifier. Alternatively, it is possible to prepare concentrates comprising active ingredient, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, for example coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentration of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The compounds I according to the invention can, for example, be formulated as follows:

I 20 parts by weight of the compound No. 1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II 20 parts by weight of the compound No. 5 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III 20 parts by weight of the compound No. 13 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV 20 parts by weight of compound No. 15 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V 3 parts by weight of the compound No. 9 are mixed with 97 parts by weight of finely divided kaolin. This gives a dust which comprises 3% by weight of active ingredient.

VI 20 parts by weight of the compound No. 27 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound No. 1 is dissolved in a mixture composed of 70 parts by weight of cyclohexanone, 20 parts by weight of ethoxylated isooctylphenol and 10 parts by weight of ethoxylated castor oil. This gives a stable emulsion.

VIII 1 part by weight of the compound No. 5 is dissolved in a mixture composed of 80 parts by weight of cyclohexanone and 20 parts by weight of Wettol® EM 31 (nonionic emulsifier based on ethoxylated castor oil). This gives a stable emulsion concentrate.

The active compounds or the herbicidal compositions can be applied pre- or post-emergence. If the active ingredients are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active ingredients reach the leaves of undesirable plants growing underneath, or the bare soil surface (post-directed, lay-by).

To widen the spectrum of action and to achieve synergistic effects, the cyclohexenone oxime ethers I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, aryl-/hetaryl-oxyalkanoic acids and their derivatives, benzoic acid and its derivatives, benzothiadiazinones, 2-aroyl-1,3-cyclohexanediones, hetaryl aryl ketones, benzylisoxazolidinones, meta-CF3-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The rates of application of active ingredient are from 0.001 to 3.0, preferably 0.01 to 1.0, kg/ha of active substance (a.s), depending on the control target, the season, the target plants and the growth stage.

The compounds of the formula I according to claim 1 can be prepared for example by reacting a hydroxylamine of the formula III with a ketone of the formula II. The ketones II in turn are accessible by oxidation (epoxidation) of a dihydropyrane of the formula IV.

The known hydroxylamines III can be prepared as described in Houben-Weyl (1971) 10/1 p.1181, or in EP-A 465 089 and DE-A 42 04 203. The dihydropyranes IV are accessible by a method similar to the procedure given in the Preparation Examples 1a) and 1b). A general review of synthetic routes to cyclohexane-1,3-diones substituted in position 5 is given in EP 142 741.

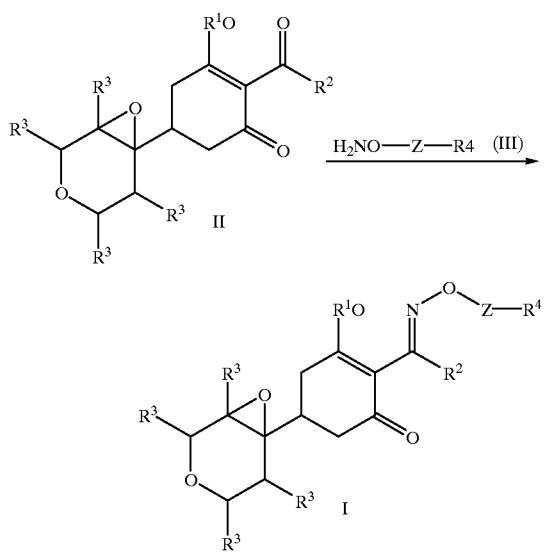

The reaction of the ketones II to give the oximes I can be carried out in the presence or absence of a solvent. As a rule, the choice of solvent is not critical, and most conventional solvents can be used. Suitable solvents are inter alia alcohols such as methanol or ethanol, or ethers such as tetrahydrofuran or methyl tert-butyl ether.

Instead of the free hydroxylamines, salts thereof, in particular the hydrochloride, may be used. In this instance, the addition of 0.5 to 2 equivalents of base promotes the conversion.

Suitable bases are, for example, alkali metal carbonates, bicarbonates or hydroxides or tertiary amines such as, for example, triethylamine, morpholine or pyridine. To obtain a homogeneous reaction mixture, water may be added as cosolvent, if appropriate.

The reaction temperature is generally from −20 to 100° C., preferably from 15 to 70° C.

In general, 0.7 to 5 equivalents and preferably 1 to 2 equivalents of the hydroxylamine III are employed per equivalent of ketone II.

Suitable oxidizing agents for oxidizing the dihydropyrans IV to the ketones II are the oxidizing agents for epoxidations described in the literature (cf. for example organikum, Barth Verlagsgesellschaft, 19th edition, 1993, p. 272).

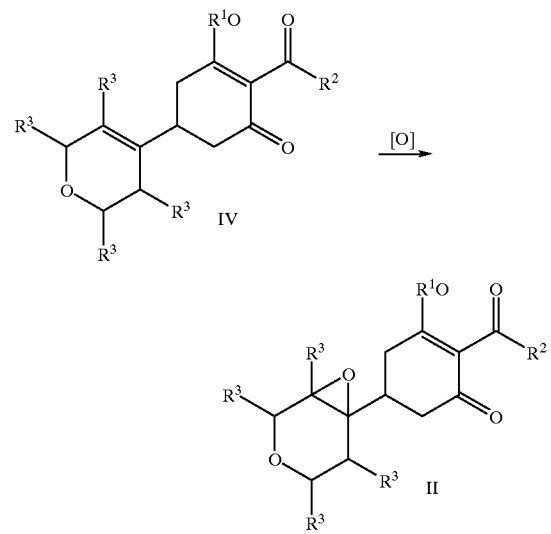

Suitable oxidizing agents are, for example, peroxides such as meta-chloroperbenzoic acid, peracetic acid, performic acid or hydrogen peroxide.

In principle, all solvents that do not interfere with the reaction can be used. Suitable solvents are, for example, halogenated hydrocarbons such as methylene chloride, dichloroethane or chloroform. Organic acids such as acetic acid or formic acid may also be used.

The reaction temperature is from −20° C. to 140° C., preferably from 10° C. to 100° C.

As a rule, 1 to 5 equivalents, preferably 1 to 2 equivalents, of the oxidizing agent are used per equivalent of dihydropyran IV. Particular preference is given to using equimolar amounts of the oxidizing agent.

The reaction of the compounds I where $R^1$ is hydrogen to the salts having agriculturally useful cations is described, for example, in EP-A 728 753.

The esterification of the compounds I where $R^1$ is hydrogen with alkylcarboxylic acids, alkylsulfonic acids and alkylphosphonic acids can be carried out in a customary manner (cf. for example Organikum, Barth Verlagsgesellschaft, 19th edition, 1993, p. 419–424).

As a rule, the 5-(dioxabicyclohept-6-yl)cyclohexenone oxime ethers I are obtained as (R/S) enantiomer or diastereomer mixtures, sometimes also as E/Z isomer mixtures, in the preparation. If desired, these isomer mixtures can be separated using customary methods such as, for example, chromatography or crystallization.

PREPARATION EXAMPLES 1) 2-[1-((E)-3-Chloroallyloxyimino)propyl]-5-(3,6-dihydro-2H-pyran-4-yl)-3-hydroxycyclohex-2-enone (Table 1, No. 15)

a) 4-(3,6-Dihydro-2H-pyran-4-yl)but-3-en-2-one: 59.4 g (0.31 mol) of diethyl (2-oxopropyl)phosphonate and 69.0 g (0.50 mol) of potassium carbonate were precharged in 75 ml of water and 40.0 g (0.25 mol) of 3,6-dihydro-2H-pyran-4-carbaldehyde (69% pure) were added dropwise at room temperature. After stirring for 24 h, the mixture was mixed with water, the phases were separated and the aqueous phase was extracted repeatedly with methylene chloride. The combined organic phases were dried over magnesium sulfate, concentrated under reduced pressure and distilled fractionally. 19.3 g of 4-(3,6-dihydro-2H-pyran-4-yl)but-3-en-2-one were obtained. Boiling point: 82° C. (0.2 mbar).

b) 2-(1-Oxopropyl)-5-(3,6-dihydro-2H-pyran-4-yl)-3-hydroxycyclohex-2-enone: For further reaction, 17.0 g (0.11 mol) of 4-(3,6-dihydro-2H-pyran-4-yl)but-3-en-2-one were precharged in 100 ml of toluene and mixed at room temperature with 14.5 g (0.11 mol) of diethyl malonate. 19.8 g (0.11 mol) of a 30% strength solution of sodium methoxide in methanol were then added dropwise, and stirring was continued at 60° C. for 2 hours. During the following removal of an azeotropic mixture of methanol and toluene, the temperature was increased until pure toluene distilled over (about 110° C.) in order to completely remove the methanol. After cooling to 60° C., the mixture was admixed with 1.2 g (10 mmol) of 4-(N,N-dimethylamino)pyridine and 10.2 g (0.11 mol) of propionyl chloride and stirred at 80° C. for 7 h. After cooling to 30° C., the mixture was washed with 50 ml of 2.5% strength sulfuric acid, and the product was then extracted with 100 g (0.25 mol) of 10% strength aqueous sodium hydroxide solution. The aqueous extract was stirred at 40–45° C. for 2 h and, after the addition of 75 ml of toluene, acidified to pH 2 using concentrated sulfuric acid. The mixture was stirred for two hours at 45–50° C. and the organic phase was separated off and washed with a little dilute sodium bicarbonate solution.

The solution obtained was either reacted directly with the desired hydroxylamines or concentrated under reduced pressure to isolate the product.

c) 2-(1-Oxopropyl)-5-(3,7-dioxabicyclo[4.1.0]hept-6-yl)-3-hydroxycyclohex-2-enone: 20 g (80 mmol) of 2-(1-oxopropyl)-5-(3,6-dihydro-2H-pyran-4-yl)-3-hydroxycyclohex-2-enone in 150 ml of methylene chloride were treated with 32.6 g (0.10 mol) of 55% strength meta-chloroperbenzoic acid, and the mixture was stirred at room temperature for 3 days. After concentration under reduced pressure at room temperature, the residue was chromatographed over silica gel using cyclohexane/ethyl acetate. Yield 14.8 g. $^1$H NMR (CDCl$_3$): $\delta$=1.15 (t); 1.95 (m); 2.30–2.80 (m); 3.07 (q); 3.13 (m); 3.50 (m); 3.98 (m); 18.2 (s).

d) 2-(1-((E)-3-Chloro-2-propenyloxyimino)propyl)-5-(3,7-dioxabicyclo[4.1.0]hept-6-yl)-3-hydroxycyclohex-2-enone: 7.9 g (29.5 mmol) of 2-(1-oxopropyl)-5-(3,7-dioxabicyclo[4.1.0]-hept-6-yl)-3-hydroxycyclohex-2-enone in 20 ml of methanol were mixed at room temperature with 3.5 g (32.4 mmol) of O-((E)-3-chloro-2-propenyl) hydroxylamine, and the mixture was stirred for about 10 hours. Concentration under reduced pressure gave an oil in quantitative yield which could be purified by chromatography over silica gel using cyclohexane/ethyl acetate. Yield 6.6 g. $^1$H NMR (CDCl$_3$): $\delta$=1.13 (t); 1.93 (m); 2.20–2.75 (m); 2.90 (m); 3.13 (m); 3.50 (m); 3.98 (m); 4.52 (d); 6.10 (m); 6.35 (d); 14.3 (s).

2) 2-(1-(2-(4-Chlorophenoxy)ethoxyimino)propyl)-5-(3,7-dioxabicyclo[4.1.0]hept-6-yl)-3-hydroxycyclohex-2-enone (Table 1, No. 1)

Physical data: $^1$H NMR (CDCl$_3$): $\delta$=1.10 (t); 1.95 (t); 2.25–2.75 (m); 2.90 (m); 3.15 (m); 3.55 (m); 4.00 (m); 4.23 (t); 4.45 (t); 6.88 (d); 7.25 (d).

3) 2-(1-(2-(4-Chlorophenoxy)propoxyimino)propyl)-5-(3,7-dioxabicyclo[4.1.0]hept-6-yl)-3-hydroxycyclohex-2-enone (Table 1, No. 5)

Physical data: $^1$H NMR (CDCl$_3$): $\delta$=1.10 (t); 1.37 (d); 1.95 (t); 2.20–2.75 (m); 2.85 (m); 3.15 (m); 3.55 (m); 4.00 (m); 4.23 (m); 4.68 (m); 6.88 (d); 7.25 (d).

4) 2-(1-(Ethoxyimino)propyl)-5-(3,7-dioxabicyclo[4.1.0]hept-6-yl)-3-hydroxycyclohex-2-enone (Table 1, No. 9)

Physical data: $^1$H NMR (CDCl$_3$): $\delta$=1.13 (t); 1.33 (t); 1.95 (t); 2.25–2.75 (m); 2.95 (m); 3.15 (m); 3.54 (m); 3.98 (m); 4.12 (q).

5) 2-(1-(3-Propenyloxyimino)propyl)-5-(3,7-dioxabicyclo[4.1.0]hept-6-yl)-3-hydroxycyclohex-2-enone (Table 1, No. 13)

Physical data: $^1$H NMR (CDCl$_3$): $\delta$=1.13 (t); 1.95 (t); 2.25–2.75 (m); 2.93 (m); 3.13 (m); 3.55 (m); 3.98 (m); 4.53 (d); 5.38 (m); 5.95 (m).

6) 2-(1-(2-(2,4-Difluorophenoxy)propoxyimino)propyl)-5-(3,7-dioxabicyclo[4.1.0]hept-6-yl)-3-hydroxycyclohex-2-enone (Table 1, No. 27)

Physical data: $^1$H NMR (CDCl$_3$): $\delta$=1.11 (t); 1.35 (d); 1.95 (t); 2.20–2.70 (m); 2.85 (m); 3.13 (m); 3.50 (m); 4.00 (m); 4.23 (m); 4.55 (m); 6.70–7.05 (m).

Further cyclohexenone oxime ethers of the formula I which have been prepared or are preparable in the same manner are listed in the table below:

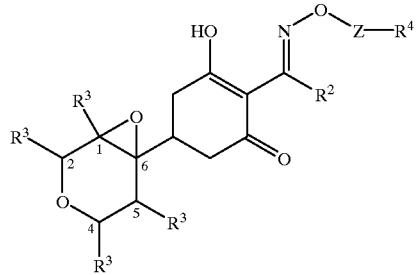

| No. | R$^2$ | R$^3$ | Z | R$^4$ |
|---|---|---|---|---|
| 1 | C$_2$H$_5$ | H | —(CH$_2$)$_2$—O— | 4-Cl-phenyl |
| 2 | n-C$_3$H$_7$ | H | —(CH$_2$)$_2$—O— | 4-Cl-phenyl |
| 3 | C$_2$H$_5$ | H | —(CH$_2$)$_2$—O— | 4-F-phenyl |
| 4 | n-C$_3$H$_7$ | H | —(CH$_2$)$_2$—O— | 4-F-phenyl |
| 5 | C$_2$H$_5$ | H | —CH$_2$CH(CH$_3$)—O— | 4-Cl-phenyl |
| 6 | n-C$_3$H$_7$ | H | —CH$_2$CH(CH$_3$)—O— | 4-Cl-phenyl |
| 7 | C$_2$H$_5$ | H | —CH$_2$CH(CH$_3$)—O— | 4-F-phenyl |
| 8 | n-C$_3$H$_7$ | H | —CH$_2$CH(CH$_3$)—O— | 4-F-phenyl |
| 9 | C$_2$H$_5$ | H | C$_2$H$_4$ | H |
| 10 | n-C$_3$H$_7$ | H | C$_2$H$_4$ | H |
| 11 | C$_2$H$_5$ | H | n-C$_3$H$_6$ | H |
| 12 | n-C$_3$H$_7$ | H | n-C$_3$H$_6$ | H |
| 13 | C$_2$H$_5$ | H | —(CH$_2$)CH=CH | H |
| 14 | n-C$_3$H$_7$ | H | —(CH$_2$)CH=CH | H |
| 15 | C$_2$H$_5$ | H | —(CH$_2$)CH=CH | trans-Cl |
| 16 | C$_2$H$_5$ | 1-CH$_3$ | —(CH$_2$)CH=CH | trans-Cl |
| 17 | C$_2$H$_5$ | 4-CH$_3$ | —(CH$_2$)CH=CH | trans-Cl |
| 18 | n-C$_3$H$_5$ | H | —(CH$_2$)CH=CH | trans-Cl |
| 19 | C$_2$H$_5$ | 1-CH$_3$ | —(CH$_2$)CH=CH | trans-F |
| 20 | C$_2$H$_5$ | H | —(CH$_2$)CH=CH | cis-Cl |
| 21 | n-C$_3$H$_7$ | H | —(CH$_2$)CH=CH | cis-Cl |

13

-continued

I

![Formula I structure with HO, epoxide, R³, R², N-O-Z-R⁴ substituents]

| No. | $R^2$ | $R^3$ | Z | $R^4$ |
|---|---|---|---|---|
| 22 | $C_2H_5$ | H | —$CH_2CH(CH_3)$—O— | 2-Cl-phenyl |
| 23 | n-$C_3H_7$ | H | —$CH_2CH(CH_3)$—O— | 3-Cl-phenyl |
| 24 | $C_2H_5$ | H | —$CH_2CH(CH_3)$—O— | 2-F-phenyl |
| 25 | $C_2H_5$ | H | —$CH_2CH(CH_3)$—O— | 2,4-dichlorophenyl |
| 26 | n-$C_3H_7$ | H | —$CH_2CH(CH_3)$—O— | 2,4-dichlorophenyl |
| 27 | $C_2H_5$ | H | —$CH_2CH(CH_3)$—O— | 2,4-difluorophenyl |
| 28 | $C_2H_5$ | 2-$CH_3$ | —$CH_2CH(CH_3)$—O— | 2,4-difluorophenyl |
| 29 | n-$C_3H_7$ | H | —$CH_2CH(CH_3)$—O— | 2,4-difluorophenyl |

USE EXAMPLES

The herbicidal activity of the 5-(dioxabicyclohept-6-yl)cyclohexenone oxime ethers I was demonstrated by the following greenhouse experiments:

The culture containers used were plastic pots containing loamy soil with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transluscent plastic hoods until the plants had rooted. This cover causes uniform germination of the test plants, unless this was adversely affected by the active compounds.

For the post-emergence treatment, the test plants were first grown to a plant height of 3 to 15 cm, depending on the plant habit, and only then treated with the active compounds which had been suspended or emulsified in water. The test plants for this purpose were either sown directly or grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

14

EXAMPLE 1

Selective herbicidal activity in post-emergence application in the greenhouse.

The rate of application was 62.5 g of a.s./ha.

The plants used in the greenhouse experiments belonged to the following species:

| Scientific name | Common name |
|---|---|
| Crop | |
| Glycine max | soybeans |
| Harmful plants | |
| Echinochloa crus-galli | barnyardgrass |
| Setaria faberii | giant foxtail |

The results showed that the abovementioned grasses can be controlled very effectively (>90% damage of the plants) using the compounds No. 15, while soybean crops suffered no visible damage by the treatment.

EXAMPLE 2

Comparative experiment with respect to EP-A 230 235

In a further experiment, the herbicidal activity of the compound No. 15 according to the invention was studied in comparison to the compound A known from EP-A 230 235 (see Table 4, Example 401).

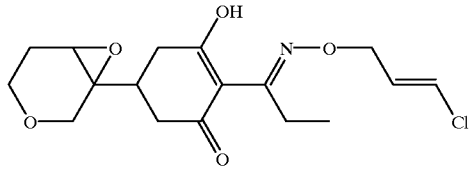

The rates of application for the post-emergence method were 31.2 g of a.s./ha or 15.6 g of a.S./ha.

In addition to the plants listed in Use Example 1, the following plant was used in this experiment

| Abbrev. | Scientific name | Common name |
|---|---|---|
| ALOMY | Alopecurus myosuroides | blackgrass |

TABLE 2

Comparison of results from greenhouse experiments

| | Application | Test plants | | |
|---|---|---|---|---|
| Comp. | rate (g of a.S./ha) | ALOMY | Echinochloa crus-galli | Setaria faberii |
| No. 15 | 31.2 | 98 | 90 | 95 |
| A | 31.2 | 60 | 80 | 98 |
| No. 15 | 15.6 | 98 | 85 | 90 |
| A | 15.6 | 0 | 50 | 80 |

As can be seen from Table 2, compound No. 15 has a considerably higher activity against the abovementioned harmful plants than comparative substance A.

We claim:

1. 5-(Dioxabicyclohept-6-yl)cyclohexenone oxime ethers of the formula I

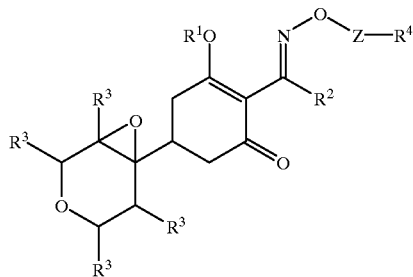

where
- $R^1$ is hydrogen, the equivalent of an agriculturally useful cation, $C_1-C_{10}$-alkylcarbonyl, $C_1-C_{10}$-alkylsulfonyl, $C_1-C_{10}$-alkylphosphonyl, benzoyl, benzenesulfonyl or benzenephosphonyl, where the last three radicals may additionally carry 1 to 5 halogen atoms;
- $R^2$ is $C_1-C_6$-alkyl;
- $R^3$ is in each case, independently of the others, hydrogen or $C_1-C_4$-alkyl;
- Z is a $C_1-C_6$-alkylene, $C_3-C_6$-alkenylene or $C_3-C_6$-alkynylene chain which may carry an exo-methylene substituent ($=CH_2$) and/or in each case one to three additional substituents selected from the group consisting of $C_1-C_3$-alkyl substituents and halogen atoms,
  is a $C_3-C_6$-alkylene or $C_4-C_6$-alkenylene chain which may carry one to three $C_1-C_3$-alkyl substituents and which contains, in addition to methylene or methine units, one of the following bridge members: oxygen, sulfur, —SO—, —SO$_2$— or —N(R$^i$)—, where R$^i$ is hydrogen, $C_1-C_4$-alkyl, $C_3-C_6$-alkenyl or $C_3-C_6$-alkynyl;
- $R^4$ is hydrogen, halogen or phenyl, where the phenyl group may be unsubstituted, partially or fully halogenated and may carry, if it is not fully halogenated, one or three substituents selected from the group consisting of nitro, cyano, formyl, halogen, $C_1-C_4$-alkyl, $C_1-C_4$-haloalkyl, $C_1-C_4$-alkoxy, $C_1-C_4$-haloalkoxy, $C_3-C_6$-alkenyl, $C_3-C_6$-alkenyloxy, $C_3-C_6$-alkynyl, $C_3-C_6$-alkynyloxy and —NR$^5$R$^6$, where
- $R^5$ is $C_1-C_4$-alkyl, $C_3-C_6$-alkenyl or $C_3-C_6$-alkynyl and
- $R^6$ is $C_1-C_4$-alkyl, $C_3-C_6$-alkenyl, $C_3-C_6$-alkynyl, $C_1-C_6$-acyl or benzoyl, which may carry one to three additional substituents selected from the group consisting of nitro, cyano, halogen, $C_1-C_4$-alkyl, $C_1-C_4$-haloalkyl, $C_1-C_4$-alkoxy and $C_1-C_4$-alkylthio.

2. 5-(Dioxabicyclohept-6-yl)cyclohexenone oxime ethers of the formula I where
- $R^1$ is hydrogen or the equivalent of an agriculturally useful cation;
- $R^2$ is ethyl or n-propyl and
- $R^3$ is hydrogen.

3. 5-(Dioxabicyclohept-6-yl)cyclohexenone oxime ethers of the formula I where
- Z is a $C_2-C_6$-alkylene or $C_4-C_6$-alkenylene chain which may carry one to three $C_1-C_3$-alkyl substituents and which, in the case of being a $C_3-C_6$-alkylene or $C_4-C_6$- alkenylene chain, may, in addition to methylene or methine units, contain an oxygen atom as bridge member;
- $R^4$ is hydrogen, halogen or phenyl which may be mono- or dihalogenated.

4. A composition comprising a herbicidally active amount of at least one 5-(dioxabicyclohept-6-yl)cyclohexenone oxime ether of the formula I as claimed in claim 1 and at least one inert liquid and/or solid carrier and, if desired, at least one surfactant.

5. A composition comprising a growth-regulating amount of at least one 5-(dioxabicyclohept-6-yl)cyclohexenone oxime ether of the formula I as claimed in claim 1 and at least one inert liquid and/or solid carrier and, if desired, at least one surfactant.

6. A process for preparing 5-(dioxabicyclohept-6-yl) cyclohexenone oxime ethers of the general formula I as claimed in claim 1, which comprises reacting an hydroxylamine of the formula III

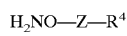

with a ketone of the formula II

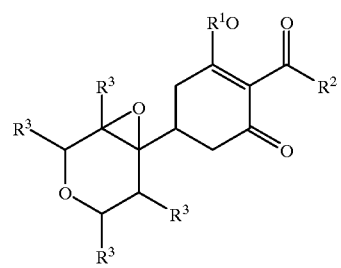

7. A process for preparing the ketones of the formula II as claimed in claim 6, which comprises allowing an oxidizing agent suitble for epoxidation to act on the dihydropyrans of the formula IV

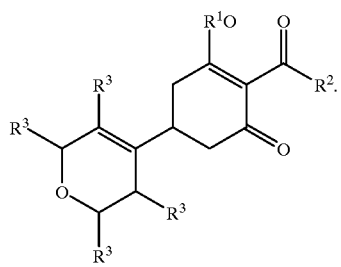

8. Ketones of the formula II where $R^1$ to $R^3$ are as defined in claim 1.

9. A method for controlling undesirable vegetation, which comprises allowing a herbicidally active amount of a 5-(dioxabicyclohept-6-yl)cyclohexenone oxime ether of the formula I as claimed in claim 1 to act on the plants and/or their habitat.

* * * * *